United States Patent
Steffan et al.

(10) Patent No.: US 6,463,171 B1
(45) Date of Patent: Oct. 8, 2002

(54) AUTOMATIC DEFECT RESIZING TOOL

(75) Inventors: Paul J. Steffan, Elk Grove; Allen S. Yu, Fremont, both of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/345,174

(22) Filed: Jun. 30, 1999

(51) Int. Cl.[7] .................................................. G06K 9/00
(52) U.S. Cl. ........................ 382/149; 382/145; 382/144; 382/194; 382/192; 382/286; 382/298
(58) Field of Search .................................. 382/141, 145, 382/149, 144, 151, 286, 194, 192, 298

(56) References Cited

U.S. PATENT DOCUMENTS

| | | | | |
|---|---|---|---|---|
| 5,544,256 A | * | 8/1996 | Brecher et al. | 382/149 |
| 5,808,735 A | * | 9/1998 | Lee et al. | 356/237.2 |
| 5,966,459 A | * | 10/1999 | Chen et al. | 382/149 |
| 6,324,298 B1 | * | 11/2001 | O'Dell et al. | 382/149 |

* cited by examiner

Primary Examiner—Phuoc Tran
Assistant Examiner—Ali Bayat
(74) Attorney, Agent, or Firm—H. Donald Nelson

(57) ABSTRACT

A method of analyzing and classifying defects on a semiconductor wafer during a semiconductor manufacturing process using an automatic defect resizing tool to accurately measure the sizes of defects.

2 Claims, 2 Drawing Sheets

AUTOMATIC DEFECT RESIZING TOOL

BACKGROUND OF THE INVENTION

1. Field of the Invention

This invention relates generally to the manufacture of high performance semiconductor devices. More specifically, this invention relates to the manufacture and the detection and classification of defects during the manufacture of high performance semiconductor devices. Even more specifically, this invention relates to the manufacture and the detection and classification of defects during the manufacture of high performance semiconductor devices utilizing an automatic defect resizing tool.

2. Discussion of the Related Art

In order to remain competitive, a semiconductor manufacturer must continuously increase the performance of the semiconductor integrated circuits being manufactured and at the same time, reduce the cost of the semiconductor integrated circuits being manufactured. Part of the increase in performance and in the reduction in cost of the semiconductor integrated circuits being manufactured is accomplished by shrinking the semiconductor device dimensions and by increasing the number of circuits per unit area on an integrated circuit chip. Another part of reducing the cost of a semiconductor chip is to increase the manufacturing yield. As is known in the semiconductor manufacturing art, the yield of chips (also known as die) from each wafer is not 100% because of defects during the manufacturing process. The number of good chips obtained from a wafer determines the yield and, as can be appreciated, chips that are discarded because of a defect or defects increases the cost of the remaining usable chips because the cost of manufacturing is amortized over the remaining usable chips.

A single semiconductor chip requires numerous processing steps during its manufacture. These steps include processing steps such as deposition of materials, implantation of ions, oxidation, etching, metallization and wet chemical cleaning. Typically, these processing steps involve placing the wafer on which the semiconductor chips are being manufactured into different tools during each of the processing steps. The optimization of each of these processing steps requires an understanding of a variety of chemical reactions and physical processes in order to produce high performance, high yield circuits. The ability to view and characterize the surface and interface layers of semiconductor chips in terms of their morphology, chemical composition and distribution is an invaluable aid to those involved in research and development, process, problem solving, and failure analysis of the resulting integrated circuits. A major part of the analysis process is to capture (detect) defects, properly classify the defects, and to analyze the defects completely to determine what caused the defects and to eliminate or avoid the cause of the defects.

In order to be able to quickly resolve process or equipment issues in the manufacture of semiconductor products, a great deal of time, effort and money is being expended by semiconductor manufacturers to capture and classify silicon based defects. Once a defect is caught and properly described and classified, work can begin to resolve the cause of the defect and to eliminate or avoid the cause of the defect. One of the biggest problems that faced semiconductor manufacturers was the inability of human inspectors to uniformly classify defects consistently and without error. This problem was solved by the development of Automatic Defect Classification (ADC) systems.

One ADC system for automatically classifying defects includes the following methodological sequence. View an image of a defect in an ADC Review Tool and assign values to elemental descriptor terms called predicates that are general descriptors such as roundness, brightness, color, hue, graininess, etc. Assign a classification code to the defect based upon the values of all the predicates. A typical ADC system can have 40 or more quantifiable qualities and properties that are considered predicates. Each predicate can have a specified range of values and a typical predicate can have a value assigned to it between 1 and 256. A value of 1 indicates that none of the value is present and a value of 256 indicates that the quality represented by the predicate is ideal. For example, a straight line would have a value of for the predicate indicating roundness, whereas a perfect circle would have a value of 256 for the same predicate.

A great enabler in the field of defect capture and analysis and the use of ADC systems has been the creation of Defect Management Systems (DMS). These DMS systems relationally associate defects with product/layer/wafer locations allowing the recapture of these defects on various analytical tools, as well as yield or trend analysis with other process related events. Increasingly, analysis tools, such as FIB (fixed ion beam) and SEM/EDS (scanning electron microscopes/energy dispersive spectroscopy) tools have been used in the manufacturing environment and images generated by these tools are routinely appended to these defects as image files. This has enhanced the ability of yield or process experts to quickly view images and/or spectra that would normally be kept in a folder that is retrievable manually.

The ADC system determines the classification code for each defect from the combination of all the predicate values assigned to the defect. The goal of an ADC system is to be able to uniquely describe all the defect types in such a manner that a single classification code can be assigned to a defect which is differentiated from all other defect types. This is accomplished by a system administrator who programs an artificial intelligence system to recognize various combinations and permutations of the 40 or more predicates to assign the same classification code to the same type of defect. This would result in a highly significant statistical confidence in the probability that the defect and all other defects of the same type or class will always be assigned the same classification code by the ADC system. These predicate values from the ADC system are stored in a database by the DMS.

The information in the DMS controlled database is retrievable for various purposes, including further processing, analysis, off-line viewing, and charting. The properly classified defects are then viewed via Pareto charts to determine, on a macro level, the current level of defectivity for various defect types.

As the dimensions of the device geometry continue to shrink, it is becoming increasingly important to ascertain an accurate defect size associated with a specific type of defect. The accurate sizing information is critical for many of the post analysis tools for the determination of parametrics that include critical area, kill ratio, and defect to tool matching.

Currently, wafers are scanned at the current level by optical or laser-scanning tools that perform such tasks including detecting defects, noting x-y location, and estimating size. Although a great deal of faith is placed on the estimated size of defects, it is notoriously inaccurate and can and has lead to erroneous conclusions. Current methods of sizing include returning sizing values as a function of greatest x-chord, or x-max multiplied by y-max, or as a constant multiplied by scattered light intensity. Analysts are very hesitant to trust the results from the present methods of determining sizes of defects.

Therefore, what is needed is a method to accurately determine the size of defects that can be used for post-analysis work.

SUMMARY OF THE INVENTION

According to the present invention, the foregoing and other objects and advantages are attained by using an automatic defect resizing tool.

In accordance with an aspect of the invention, a semiconductor wafer production lot is sent through a manufacturing process, a first layer of the wafer lot is processed, a selected inspection wafer is placed in a scan tool, defect location information is sent to a defect management system, which sends the defect location information to an automatic defect classification review tool where the automatic defect resizing tool accurately determines the sizes of the defects.

In accordance with another aspect of the invention, the sizes of the defects are determined by counting the number of pixels in each defect and multiplying the number of pixels in each defect by the magnification factor.

In accordance with another aspect of the invention, the sizes of the defects are sent to the defect management system and stored with other defect information that is made available for further analysis.

The described method thus provides a method to accurately determine the sizes of defects so that further analyses of defects are facilitated.

The present invention is better understood upon consideration of the detailed description below, in conjunction with the accompanying drawings. As will become readily apparent to those skilled in the art from the following description, there is shown and described an embodiment of this invention simply by way of illustration of the best mode to carry out the invention. As will be realized, the invention is capable of other embodiments and its several details are capable of modifications in various obvious aspects, all without departing from the scope of the invention. Accordingly, the drawings and detailed description will be regarded as illustrative in nature and not as restrictive.

BRIEF DESCRIPTION OF THE DRAWINGS

The novel features believed characteristic of the invention are set forth in the appended claims. The invention itself, however, as well as a preferred mode of use, and further objects and advantages thereof, will best be understood by reference to the following detailed description of an illustrative embodiment when read in conjunction with the accompanying drawings, wherein:

DETAILED DESCRIPTION

Reference is now made in detail to a specific embodiment of the present invention that illustrates the best mode presently contemplated by the inventors for practicing the invention.

Figure 1:
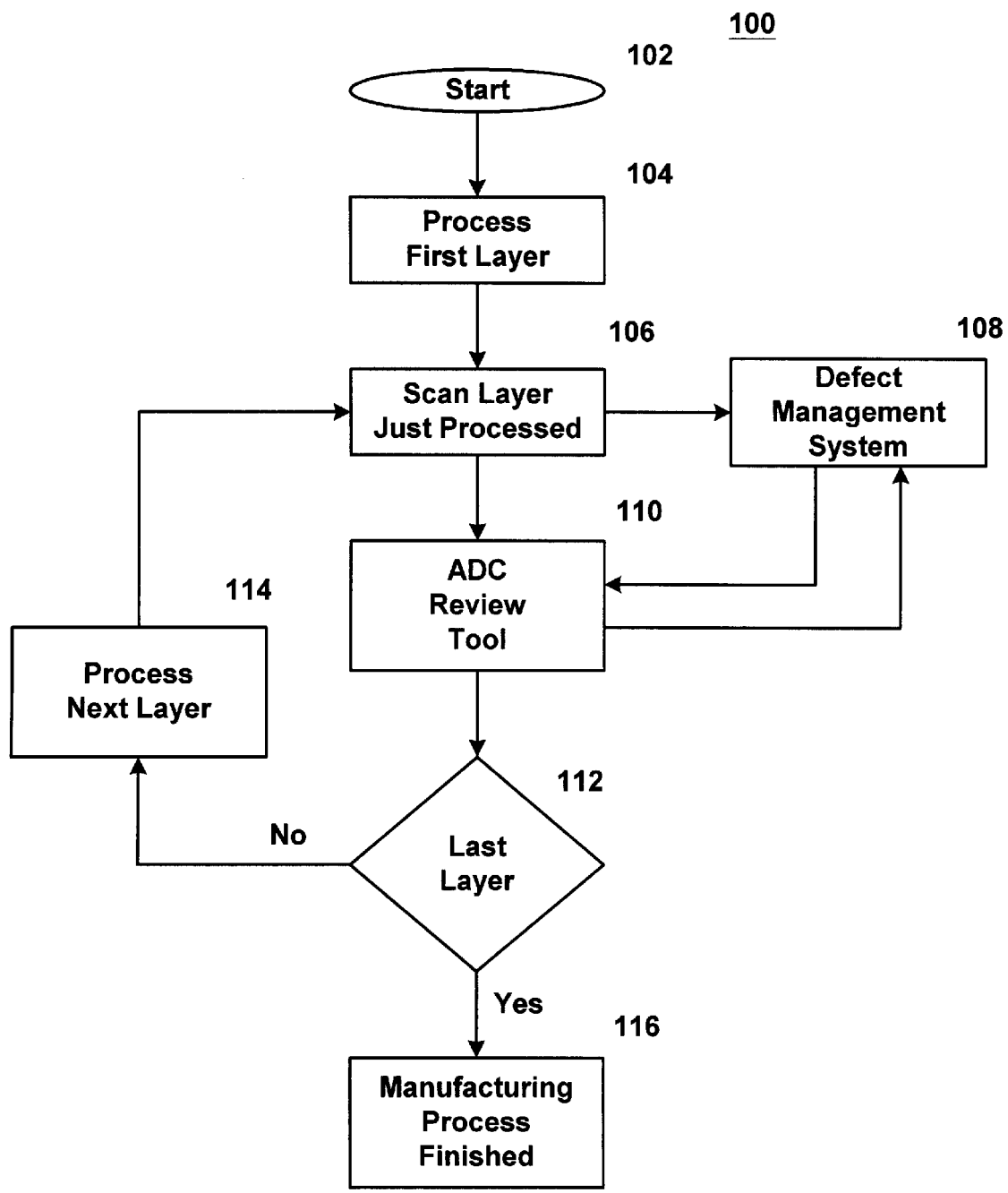
FIG. 1 is a portion of a flow diagram of a typical semiconductor manufacturing process showing the use of an ADC review tool to automatically classify defects located by a scan tool and a defect management system (DMS) that stores defect information in a database.

FIG. 1 is a portion 100 of a flow diagram of a typical semiconductor manufacturing process showing the use of an automatic defect classification (ADC) review tool to automatically classify defects located by a scan tool a defect management system (DMS) that stores defect information in a database. The defect information generated by the scan tool is stored in the database and the defect information can be sent to various review tools for review of selected defects or review of all defects. The defect information generated by the various review tools is also sent to the defect management system and is stored in the database and is available to operators to review and analyze.

A production lot of wafers is processed at one time. A production lot of wafers typically is made up of approximately 25 wafers. The manufacturing process typically involves the processing of multiple layers, however the processing of only one layer will be described herein. The portion 100 of the manufacturing process begins with a first layer, indicated at 102 and the first layer is processed at 104. After the layer is processed, a selected wafer from the production lot is placed in a scan tool at 106, which scans the selected wafer and captures defects by determining their locations. The defect location information is forwarded to a defect management system (DMS) at 108. To analyze and classify the defects, the selected wafer is placed in an automatic defect classification (ADC) review tool at 110 and the defect management system 108 sends location information for defects that are to be analyzed and classified to the ADC review tool. The ADC review tool at 110 typically analyzes defects by comparing the location of the defects in the die on which they occur to the same exact locations on adjacent die that the ADC review tool assumes are identical die. Using this information, the ADC review tool at 110 assigns a classification code to the defects. The classification codes are returned to the defect management system 108, which stores the classification codes assigned to the defects in a database.

After the ADC review tool 110 is finished analyzing and classifying the defects, it is determined at 112 whether the layer just processed is the last layer. If the layer just processed is not the last layer, the next layer is processed at 114 and the wafer is then returned to the flow at 106 and the process described above is repeated for the next layer. If it is determined at 112 that the layer just processed is the last layer, the wafer is finished as indicated at 116.

Figure 2:
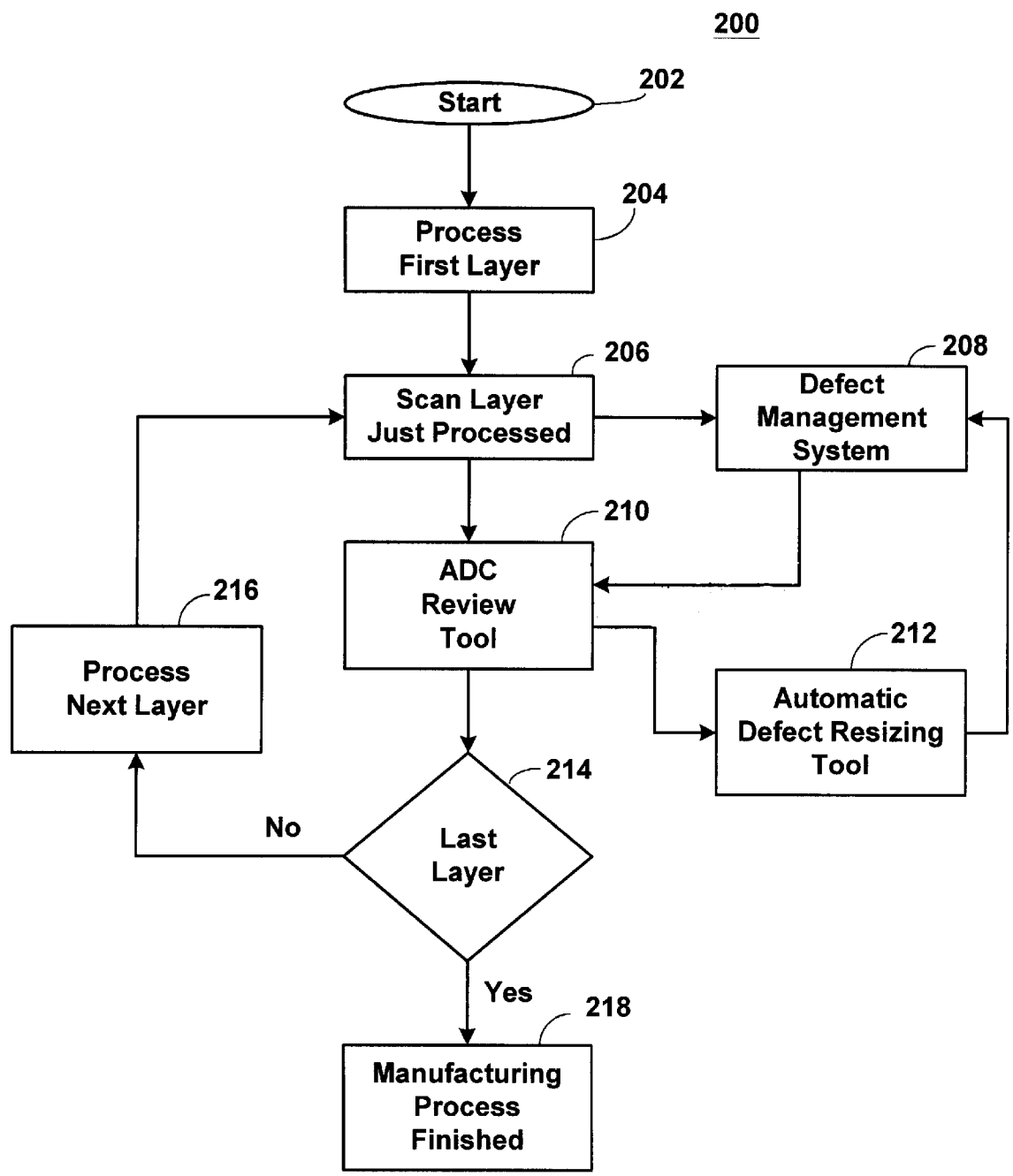
FIG. 2 is a portion of a flow diagram of a semiconductor manufacturing process in accordance with the present invention showing the use an Automatic Defect Resizing Tool that provides sizing information that is stored by the defect management system in a database.

FIG. 2 is a portion 200 of a flow diagram of a semiconductor manufacturing process in accordance with the present invention showing the use of input from an Automatic Defect Resizing Tool to the defect management system (DMS) that stores defect information in a database. The defect information generated by the scan tool is stored in the database and can be sent to various review tools for review of selected defects or review of all defects. The defect information generated by the various review tools is also sent to the defect management system and is stored in the database and is available to operators to review and analyze.

A production lot of wafers is processed at one time. A production lot of wafers typically is made up of approximately 25 wafers. The manufacturing process typically involves the processing of multiple layers, however the processing of only one layer will be described herein. The portion 200 of the manufacturing process begins with a first layer, indicated at 202 and the first layer is processed at 204. After the layer is processed, a selected wafer from the production lot is placed in a scan tool at 206, which scans the selected wafer and captures defects by determining their locations. The defect location information is forwarded to a defect management system (DMS) at 208. The defect management system 208 sends the defect location information to an automatic defect classification (ADC) review tool 210. The automatic defect classification review tool 210 analyses and classifies the defects. Currently, wafers are scanned at the current level by optical or laser scanning tools that detect defects and provides further information that includes the defects x-y locations on the wafer and estimates the size of the defects. However, as discussed above the size estimates are not sufficiently accurate to allow for meaningful further analysis.

In order to determine a more accurate size for the defects, the defect information is sent to an automatic defect-resizing tool 212. It is noted that the defect-resizing tool 212 is shown separate from the ADC Review Tool 210, however, it should be appreciated that the defect-resizing function can be incorporated into the ADC Review Tool 210. The ADC Review Tool 210 currently can pictorially isolate defects for review. In accordance with the present invention, the ADC Review Tool 210 software is modified to accurately determine the size of a defect under review by counting the number of pixels that comprise the defect and multiplying that by the magnification factor to obtain an accurate defect size.

After the ADC review tool 210 is finished analyzing and classifying the defects, it is determined at 214 whether the layer just processed is the last layer. If the layer just processed is not the last layer, the next layer is processed at 216 and the wafer is then returned to the flow at 206 and the process described above is repeated for the next layer. If it is determined at 214 that the layer just processed is the last layer, the wafer is finished as indicated at 218.

Some of the benefits of the invention include:

1. It allows all defects in the database to be resized easily and accurately.
2. It enables the ability for post-analysis with increased accuracy.
3. It improves data consistently and integrity of the database.

In summary, the results and advantages of the method of analyzing and classifying defects on a semiconductor wafer using an automatic defect resizing tool can now be more fully realized. The described method thus effectively provides a method to accurately determine the sizes of defects so that further analyses of defects are facilitated.

The foregoing description of the embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of analyzing and classifying defects on a semiconductor wafer during a semiconductor manufacturing process, the method comprising:

(a) sending a production lot of wafers through a manufacturing process;

(b) scanning a selected wafer from the production lot of wafers for defects;

(c) sending location information for defects caught during the step of scanning to a defect management system;

(d) sending the location information for defects to an automatic defect classification review tool; and (e) determining the size of each individual defect by counting the number of pixels comprising each of the individual defects and multiplying the number of pixels in each of the individual defects by the magnification factor to determine the size of each individual. defect.

2. The method of claim 1 further comprising sending the size of each individual defect to the defect management system.

* * * * *